(12) United States Patent
Ghosh

(10) Patent No.: US 6,487,902 B1
(45) Date of Patent: Dec. 3, 2002

(54) APPARATUS AND METHOD FOR BIAXIAL TENSILE TESTING OF MEMBRANE MATERIALS

(75) Inventor: Tushar K. Ghosh, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/429,114

(22) Filed: Oct. 27, 1999

(51) Int. Cl.$^7$ ................................................. G01L 5/04
(52) U.S. Cl. ........................................... 73/159; 73/826
(58) Field of Search ............................ 73/826, 90, 856, 73/794, 866.4, 818, 829, 831, 159, 160; 26/73, 89; 53/556; 526/255; 425/383; 264/161, 216; 38/102.5

(56) References Cited

U.S. PATENT DOCUMENTS

| | | | | |
|---|---|---|---|---|
| 4,096,741 A | * | 6/1978 | Sternstein | 73/90 |
| 4,192,194 A | * | 3/1980 | Holt | 73/794 |
| 5,512,229 A | * | 4/1996 | Bosse et al. | 264/161 |
| 5,905,205 A | * | 5/1999 | Clay | 73/856 |

\* cited by examiner

*Primary Examiner*—Max Noori
(74) *Attorney, Agent, or Firm*—Jenkins & Wilson, P.A.

(57) ABSTRACT

An apparatus and method for biaxial load deformation testing of textile and other membrane materials including a first pair of spaced-apart segmented clamping systems for detachably engaging a membrane test material along opposing sides in the X direction. A second pair of spaced-apart segmented clamping systems is provided for detachably engaging a membrane test material along opposing sides extending in the Y direction. Each of the first pair and each of the second pair of spaced-apart segmented clamping systems are interconnected by a pantograph so as to be slidably extendable and slidably contractible with respect to each other and proportional to strain in the membrane test material in the X and Y directions, respectively. The first and second pair of segmented clamping systems are interconnected by a linkage system such that the second pair of segmented clamping systems will slidably extend in the Y direction proportional to strain imparted to a membrane test material in the Y direction when the first pair of segmented clamping systems is caused to move apart in the Y direction, and the first pair of segmented clamping systems will slidably extend in the X direction proportional to strain imparted to a test membrane in the X direction when the second pair of clamping systems is caused to move apart in the X direction.

14 Claims, 15 Drawing Sheets

σx ———
σy - - - - -

APPARATUS AND METHOD FOR BIAXIAL TENSILE TESTING OF MEMBRANE MATERIALS

GOVERNMENT INTEREST

This invention was made with Government support under Grant No. A94-8 awarded by the Department of Commerce (National Textile Center). The Government has certain rights therein.

TECHNICAL FIELD

The present invention relates to tensile testing of membrane materials, and more particularly to an apparatus and method for biaxial tensile testing of membrane materials.

RELATED ART

Traditionally, the tensile properties of fabrics are evaluated in uniaxial testing in which force-deformation response of a fabric is measured along one of the major axes (machine or cross). Results of uniaxial tests produce indices of relative tensile behavior but are inadequate for many applications. However, in actual use, the textile fabrics rarely experience true uniaxial forces. In most instances, the forces are imposed simultaneously in more than one direction resulting in responses that are quite different from that under uniaxial force. Since most fabrics or orthotropic membranes possess two principal directions and the forces or deformations in most cases can be resolved into two orthogonal components, it is important to understand their behavior under two dimensional force or deformation. Application of forces or extensions simultaneously along two orthogonal axes is referred to as "biaxial".

Often, the objective of tensile testing of fabrics is to characterize their nature of failure in terms of breaking elongation and strength. However, for many applications it may be more important to find out the relationships between applied stresses (or strains) and resultant strains (or stresses), e.g., $$\sigma_x = f_1(\epsilon_x, \epsilon_y, \gamma_{xy}), \sigma_y = f_2(\epsilon_x, \epsilon_y, \gamma_{xy}), \sigma_{xy} = f_3(\epsilon_x, \epsilon_y, \gamma_{xy})$$

where $\sigma_x$ and $\sigma_y$ are stresses in machine and cross directions, respectively, and $\sigma_{xy}$ is the shear stress. Similarly, $\epsilon_x$ and $\epsilon_y$ are strains in machine and cross directions, and $\gamma_{xy}$ is the shear strain. These constitutive relationships between stress-strain parameters are well known for linear orthotropic materials. However, the stress-strain relationships of textile fabrics are far more complex and non-linear.

The need to measure the constitutive laws of fabric behavior, in addition to studying their nature of failure, has received considerable attention in the literature. A number of studies have been reported in the area of theoretical modeling of fabric deformation under uniaxial as well as biaxial tensile forces. Other researchers have reported various experimental methods of evaluating fabric behavior under biaxial tensile forces.

Multi-directional test devices have been described by Ariano ("Rubber Stretched by Forces in Two Directions Perpendicular to one Another", *Rubber Chemistry and Technology*, 13, 92–102 (1942)) as early as 1942. He developed a static two-dimensional tester for rubber films. Anderson ("A Method for Obtaining Stress-Strain Relations in Non-Isotropic Flexible Sheet Material Under Two-Dimensional Stress", *Journal of Scientific Instruments*, 24, 25 (1947)) and Boonstra ("Stress-Strain Properties of Natural Rubber under Biaxial Strain", *Journal of Applied Physics*, 21, 1098–1104 (1950)) used a pressure cylinder apparatus suitable for impermeable sheet materials. Treloar ("The Swelling of Cross-Linked Amorphous Polymer under Strain", *Transactions of Faraday Society*, 46, 783–789 (1950)) developed an apparatus for imposing four-directional planar strains in rubber, but without any provision for measuring forces. The two-dimensional force-extension tester reported by Reichard, Woo, and Montgomery ("A Two Dimensional Load-Extension Tester for Woven Fabrics", *Textile Research Journal*, 23, 424–4248 (1953)) and later used by Woo, Dillon, and Dusenbury ("The Reaction of Formaldehyde with Cellulosic Fibers, Part II: Mechanical Behavior", *Textile Research Journal*, 26, 761–783 (1956)) is a modified uniaxial tensile tester that was designed to extend a fabric along two perpendicular directions. However, the instrument could measure the force developed in one direction only under moderate levels of strain. Checkland. Bull, and Bakker ("A Two-Dimensional Load-Extension Tester for Fabrics and Film", *Textile Research Journal*, 28, 399–403 (1958)) reported a two-dimensional force extension tester in which a four-jaw, self-centering lathe chuck was used as the straining device. The sample size was quite small, as was the strain level.

All these devices were equipped with solid clamps that did not allow any deformation along the clamps, a critical requirement, for large or finite deformation. Additionally, none of the above investigators either defined or examined the role of control variables in interpreting their experimental results. Of the multi-directional testers already reviewed, only two were specifically designed for and readily applicable to the laboratory testing of fabrics. In both cases, the clamps were moved at constant rates to apply strains in the sample. However, as Klein ("Stress-Strain Response of Fabrics underTwo-Dimensional Loading, Part I: The FRL Biaxial Tester", *Textile Research Journal*, 29, 816–821 (1959)) pointed out, in both cases neither the forces nor the extensions are controlled in the central region of the test specimen. Thus, while general trends in biaxial behavior can be determined from these machines, considerable generality is lost and quantitative comparison of different materials is rather impossible.

Klein described a biaxial tester with solid clamps and proposed a set of design criteria for a biaxial tester based on sound theoretical analysis. He pointed out that in a biaxial testing system, either both forces or both extensions must be specified or controlled while the other should be measured. Klein chose forces as independent variables because of his particular requirements. He then concluded that a biaxial test could be considered completely controlled and reproducible by the control of a single factor, i.e., the ratio of forces or extension in the two directions. Klein designed his instrument to measure force-extension behavior of a cruciform sample (2 in.×2 in.) under different levels of force-ratio.

Freeston et al. ("Mechanics of Elastic Performance of Textile Materials, Part 18. Stress-Strain Response of Fabrics under Two Dimensional Loading", *Textile Research Journal*, 37, 948–975 (1967)) in 1967 reported a biaxial tester developed by the Air Force Materials Laboratory. The load-frame of the test system described by Freeston et al. was similar to Klein. However, the clamping system of this instrument was designed to rotate freely about an axis perpendicular to the plane of the test specimen to permit shear deformations.

An important factor to be considered in biaxial testing of fabrics or other similar membranes is the distribution of stress and strain in the test specimen. Perfect homogeneity of strain in a test device is almost always unattainable.

However, test instruments must be designed to minimize the variations of stress and strain. None of the prior art instruments described thus far allow for homogeneous distribution of stress and strain. In testing a flat specimen of a membrane/fabric, it is necessary to allow the specimen to undergo tensile strain in the direction along each clamp. In the vicinity of the solid clamps, these strains are not allowed to develop. Consequently, these "boundary effects" become particularly severe in cases of small samples.

A number of testers reported in the literature have provided for deformation along each clamp. Two of these, Rivlin et al. ("Large Elastic Deformations of Isotropic Materials, VII: Experiments on the Deformation of Rubber", *Philosophical Transactions of the Royal Society*, 243, 251–288 (1951)) and McRory et al. ("Experimental Investigation of the Biaxial Load-Extension Properties of Plain, Weft-Knitted Fabrics", *Textile Research Journal*, 47, 233–239 (1977)) applied stresses with what was essentially point contact, while Sakaguchi et al. (*Journal of the Society of Materials Science*, Japan, 17, 365 (1968)) and Kawabata et al. ("The Finite-Deformation Theory of Plain-Weave Fabrics, Part 1: The Biaxial-Deformation Theory", *Journal of The Textile Institute*, 64, 21–46 (1973) and "Nonlinear Theory of the Biaxial Deformation of a Triaxial-Weave Fabric", *Journal of The Textile Institute*) used segmented clamps of finite area. Several testers used specimens with tabs protruding from the edges in order to help induce a homogeneous stress distribution in the center of the specimen. However, the tester of McRory et al. used a specimen with straight edges, and relied upon closer spacing of the grip points (0.25 cm) to distribute the stresses. While the segmented clamping system improved the homogeneity of the strain distribution, edge effects were still present in the stress and strain measurement system. The edge effects can be reduced to some extent by measuring the stress and strain only over the central part of the specimen. However, selective measurement of stress is difficult. Kawabata et al. used the instrument mentioned earlier, but with a modification such that stress was measured only over the center sections of the sides of the specimen. This was achieved by attaching the corner clamp-grips to members other than the "load-detection-bars", to which central clamps and force transducers were attached. Riviin used another approach of individual adjustment of clamps to address this problem. It is worth observing that Sakaguchi et al. and Kawabata et al. used ratio of strain in the two directions as the control parameter of their testing as opposed to force-ratio.

While these segmented clamping systems improved the homogeneity of the strain distribution, frictional forces within the clamp segments and edge effects were still present in the system. In segmented clamps, an extension in the X-direction is accommodated by tabs in the Y-direction by pulling on the Y-direction clamp-segments laterally at an angle other than zero. In other words, the force necessary to move the Y-direction clamp-segments is provided by the X-direction clamps and transmitted through the tabs in Y-direction. Even a small frictional resistance to this movement will cause inhomogeneity in the strain field of the test sample. More importantly, it develops stress concentrations at the joining point of the adjacent Y-direction tabs, which promote tear into the test area. The same can be said about an extensional displacement of the Y-direction clamps and corresponding adjustment by the X-direction clamp-segments.

Thus, the search continues in biaxial testing for a suitable clamp system that will allow for unhindered strain to occur in a test sample, in particular, near the edges while extending the capacity of load-frames to useful levels.

DISCLOSURE OF THE INVENTION

In accordance with the present invention, applicant provides an apparatus for biaxial load deformation testing of textile and other membrane materials that provides for unhindered strain to occur in the sample near the edges so as to obviate significant "boundary effects" during deformation testing. The apparatus comprises a first pair of spaced-apart segmented clamping systems for detachably engaging a membrane test material along opposing sides extending in a first (X) direction wherein the clamping systems each comprise a plurality of clamps interconnected by a pantograph so as to be slidably extendable and slidably contractible with respect to each other. A second pair of spaced-apart segmented clamping systems is provided for detachably engaging a membrane test material along opposing sides extending in a second (Y) direction orthogonal to the first direction wherein the clamping systems each comprise a plurality of clamps interconnected by a pantograph so as to be slidably extendable and slidably contractible with respect to each other. A first drive system is used for moving the first pair of segmented clamping systems apart from each other so as to impart a predetermined strain in the second (Y) direction, and a second drive system is provided for moving the second pair of segmented clamping systems apart each from the other so as to impart a predetermined strain in the first (X) direction. A first linkage system operatively interconnecting the first and second pair of segmented clamping systems is provided so as to slidably extend the second pair of segmented clamping systems in the second (Y) direction proportional to strain imparted to a membrane test material in the second (Y) direction when the first pair of segmented clamping systems is caused to move apart in the second (Y) direction by the first drive system. Further, a second linkage system operatively interconnecting the first and second pair of segmented clamping systems is provided so as to slidably extend the first pair of segmented clamping systems in the first (X) direction proportional to strain imparted to a test membrane in the first (X) direction when the second pair of clamping systems is caused to move apart in the first (X) direction by the second drive system.

Also in accordance with the present invention, applicant provides a method for biaxial load deformation testing of textile and other membrane materials so as to provide for unhindered strain to occur in the sample near the edges during deformation. The method includes providing a first pair of spaced-apart segmented clamping systems for detachably engaging a membrane test material along opposing sides extending in a first (X) direction wherein the clamping systems each comprise a plurality of clamps pantographically interconnected so as to be slidably extendable and slidably contractible with respect to each other. The method further includes providing a second pair of spaced-apart segmented clamping systems for detachably engaging a membrane test material along opposing sides extending in a second (Y) direction orthogonal to the first direction wherein the clamping systems each comprises a plurality of clamps pantographically interconnected so as to be slidably extendable and slidably contractible with respect to each other. The method further comprises driving the first pair of segmented clamping systems apart from each other to impart a predetermined stress and/or strain in the second (Y) direction and thereby causing the operatively connected second pair of segmented clamping systems to slidably extend in the second (Y) direction proportional to the strain imparted to a membrane test material in the second (Y) direction. Finally, the method provides for driving the second pair of segmented clamping systems apart from each other to impart a predetermined stress and/or strain in the first (X) direction and thereby causing the operatively connected first pair of segmented clamping systems to slidably extend in the first (X) direction proportional to the strain imparted to a membrane test material in the first (X) direction.

It is therefore an object of the present invention to provide an apparatus and method for biaxial load deformation testing of textile and other membrane materials that allows for unhindered strain to occur near the test sample edges so as to obviate boundary effects during testing.

It is another object of the present invention to provide an apparatus and method for biaxial load deformation testing of textile and other membrane materials that utilizes segmented and self-adjusting clamping systems to engage the four edges of a test sample so as to allow for finite biaxial deformation without suffering any significant undesirable boundary effects during testing.

It is still another object of the present invention to provide an apparatus and method for biaxial load deformation testing of textile and other membrane materials which serves to minimize the stress concentrations and strain inhomogeneities during biaxial load deformation testing of textile and other membrane materials.

It is still another object of the present invention to provide an apparatus and method for biaxial load deformation testing of textile and other membrane materials that uses an improved segmented clamping system for gripping deformable membrane materials during biaxial testing thereof.

Some of the objects of the invention having been stated, other objects will become evident as the description proceeds, when taken in connection with the accompanying drawings described hereinbelow.

BEST MODE FOR CARRYING OUT THE INVENTION

Figure 1A:
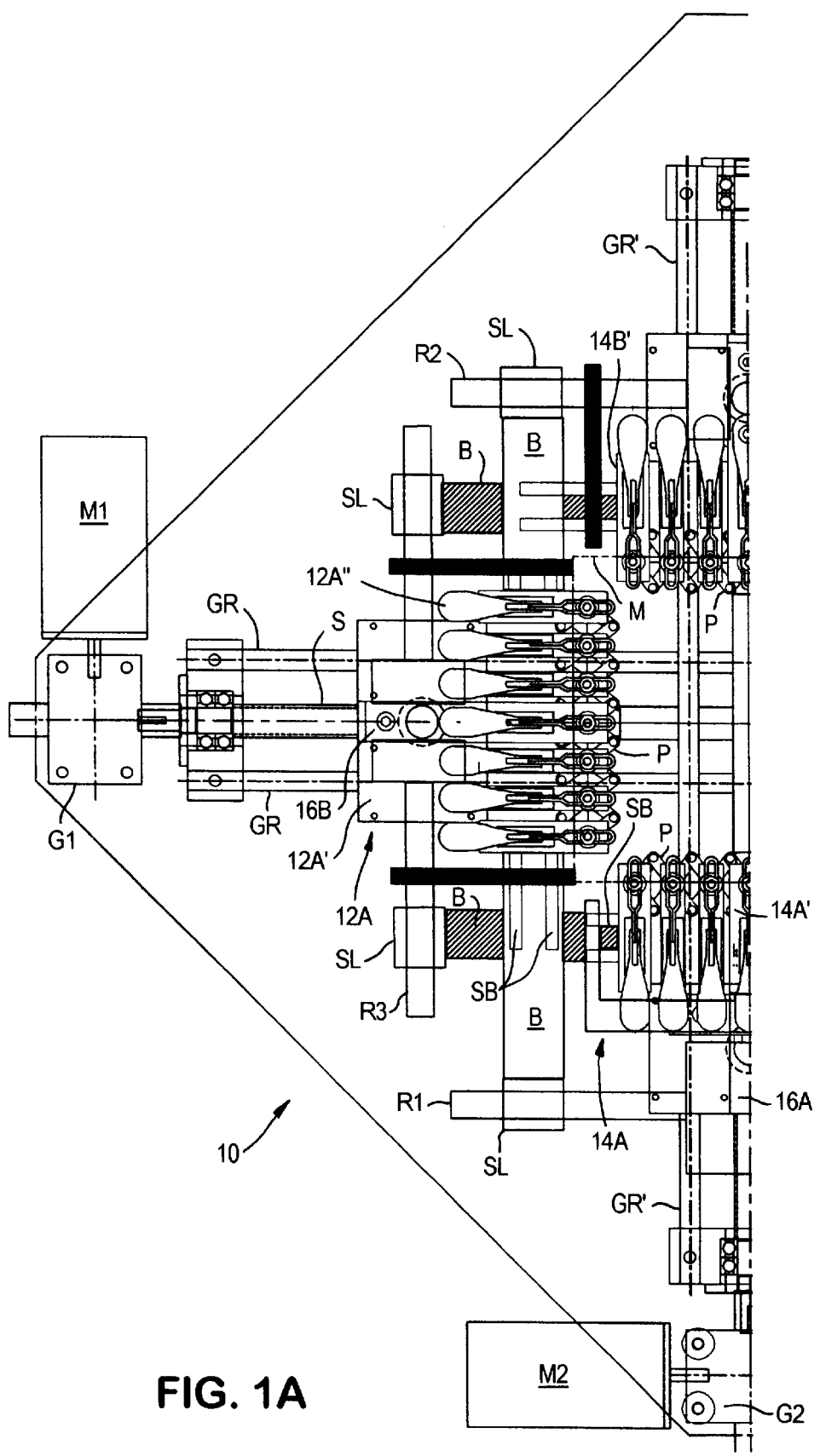
FIGS. 1A and 1B show a top plan view of the apparatus for biaxial load deformation testing of the present invention.
Figure 1B:
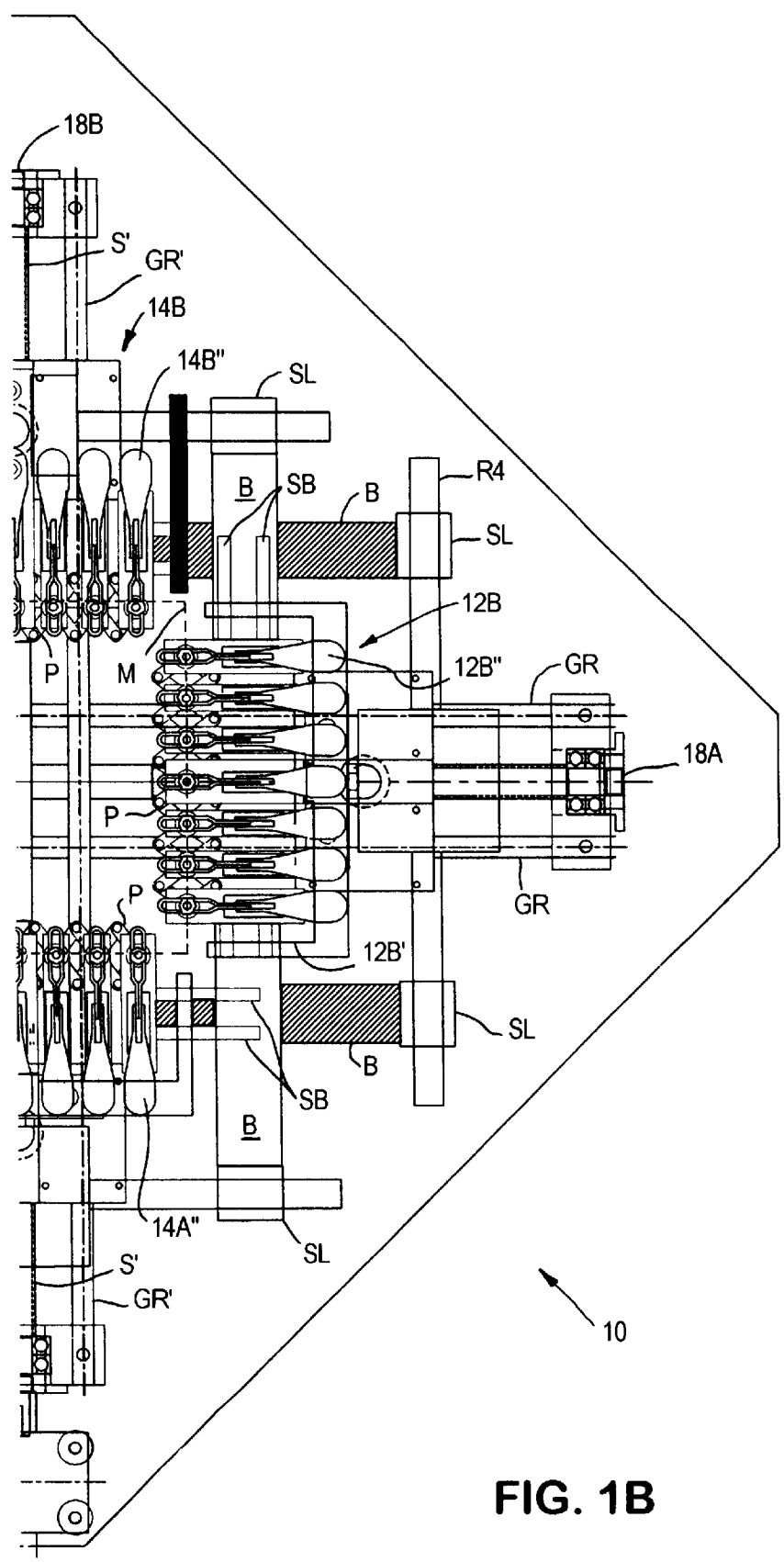
Figure 2A:
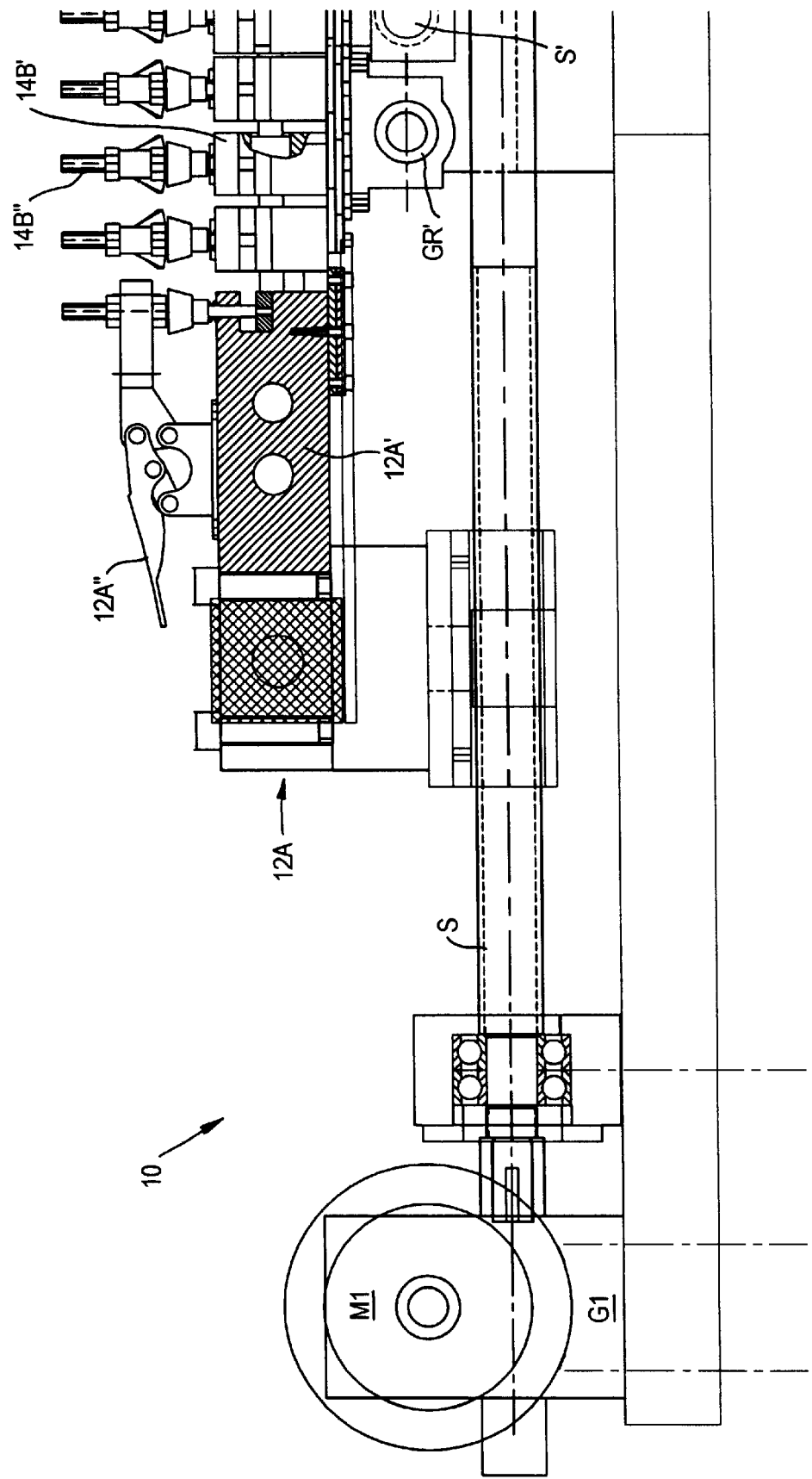
FIGS. 2A and 2B show a side elevation view of the apparatus for biaxial load deformation testing shown in FIGS. 1A and 1B.
Figure 2B:
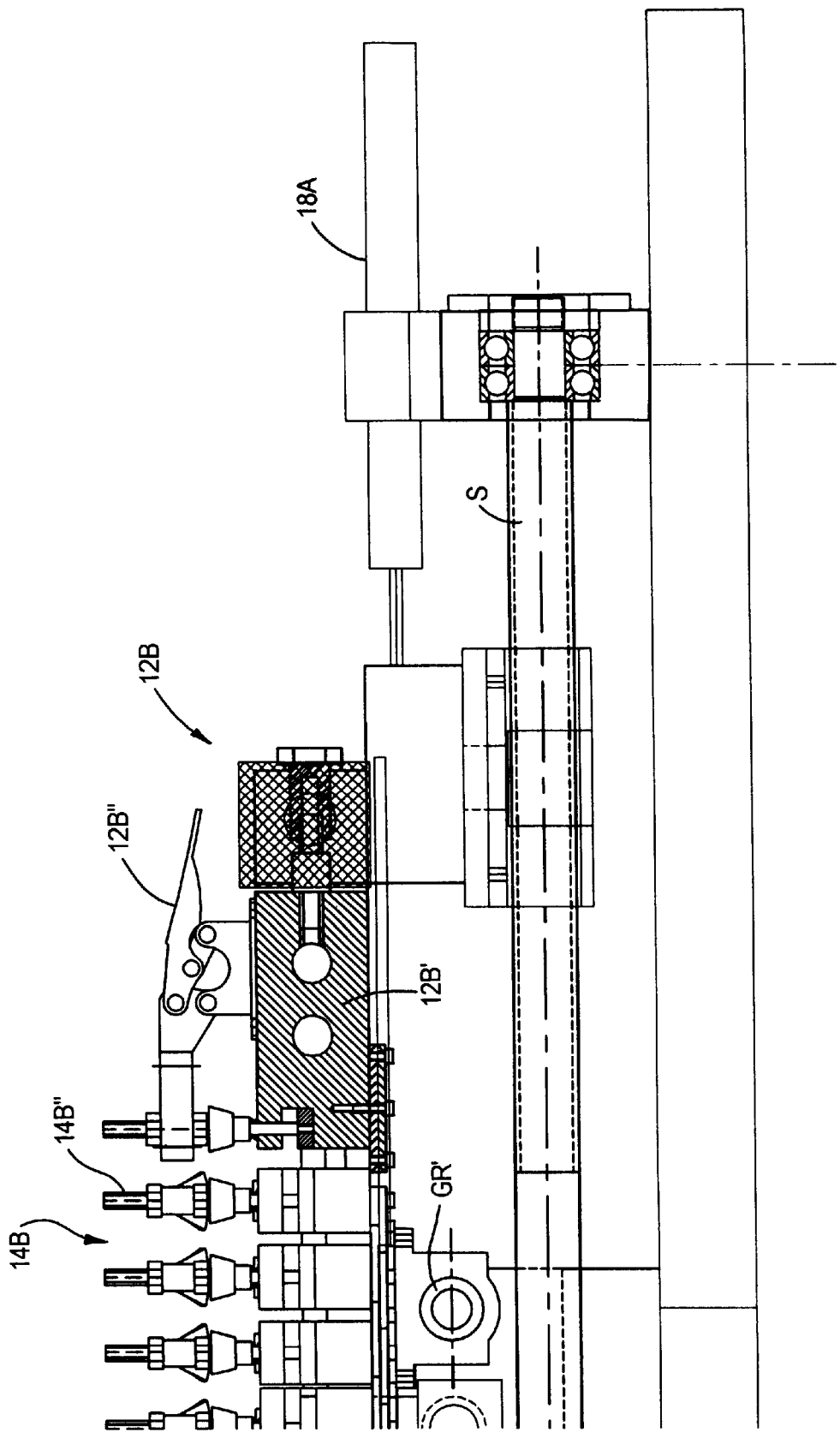
Figure 3:
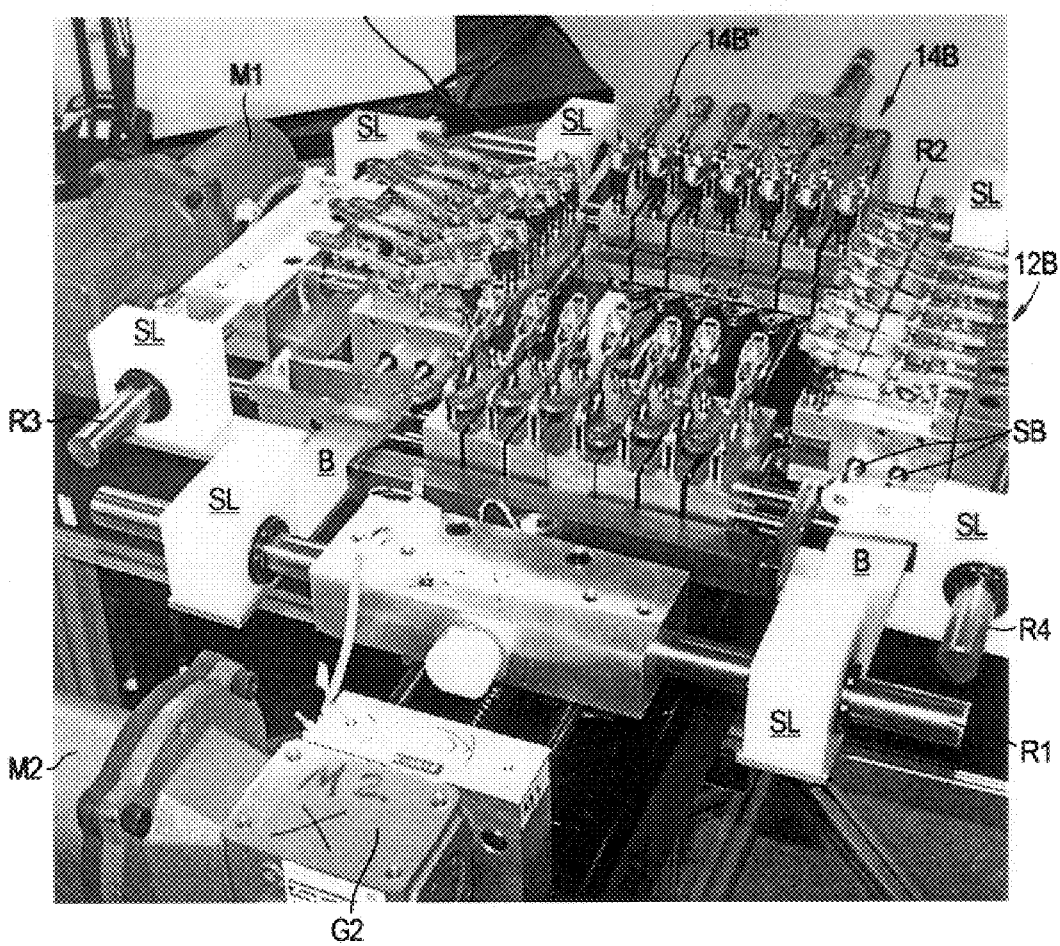
FIG. 3 is a perspective view of the apparatus for biaxial load deformation testing of the present invention.
Figure 4:
FIG. 4 is an enlarged perspective view of the motor and drive mechanism for the segmented clamping system for engaging opposing sides of a membrane test material in the X direction.
Figure 5:
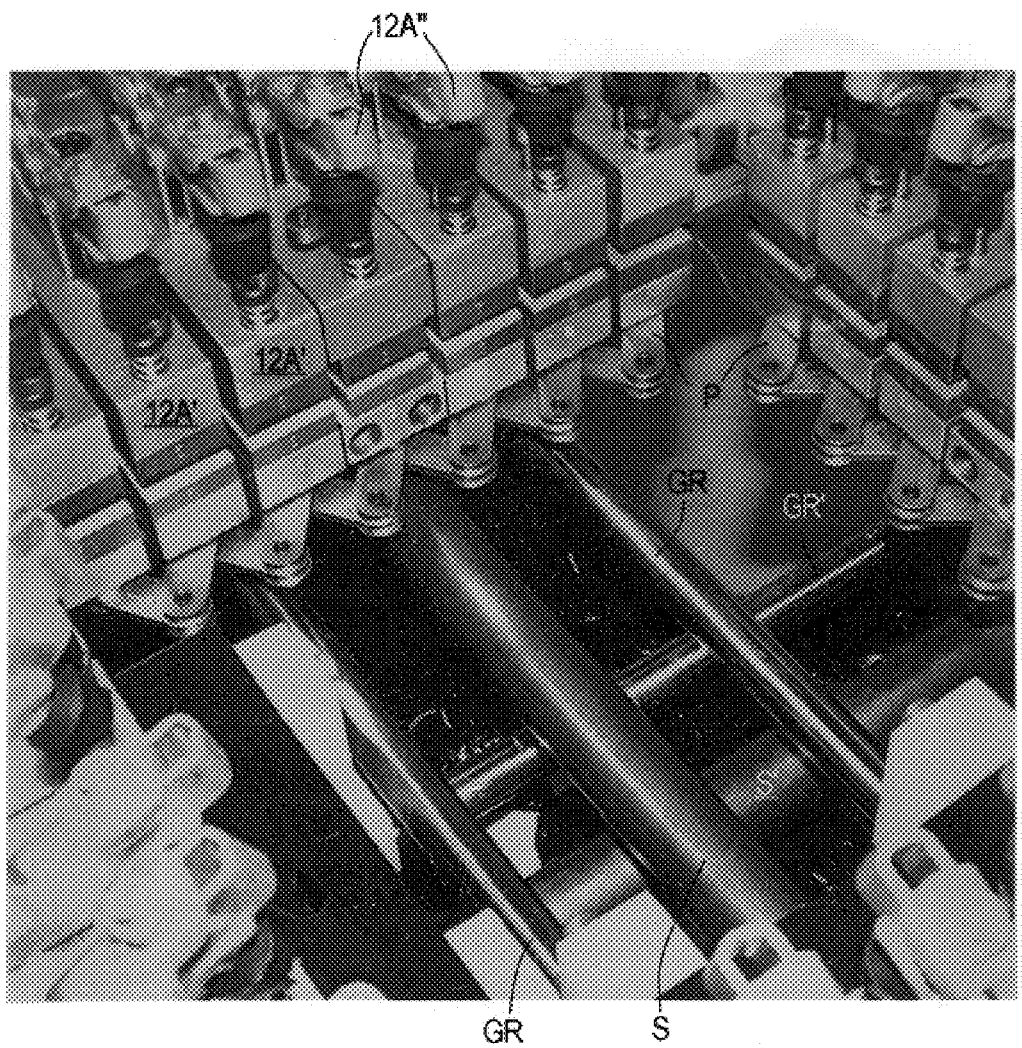
FIG. 5 is an enlarged perspective view of one set of segmented clamps extending in the X direction and depicting the interconnection of the clamp elements by the pantograph.
Figure 6:
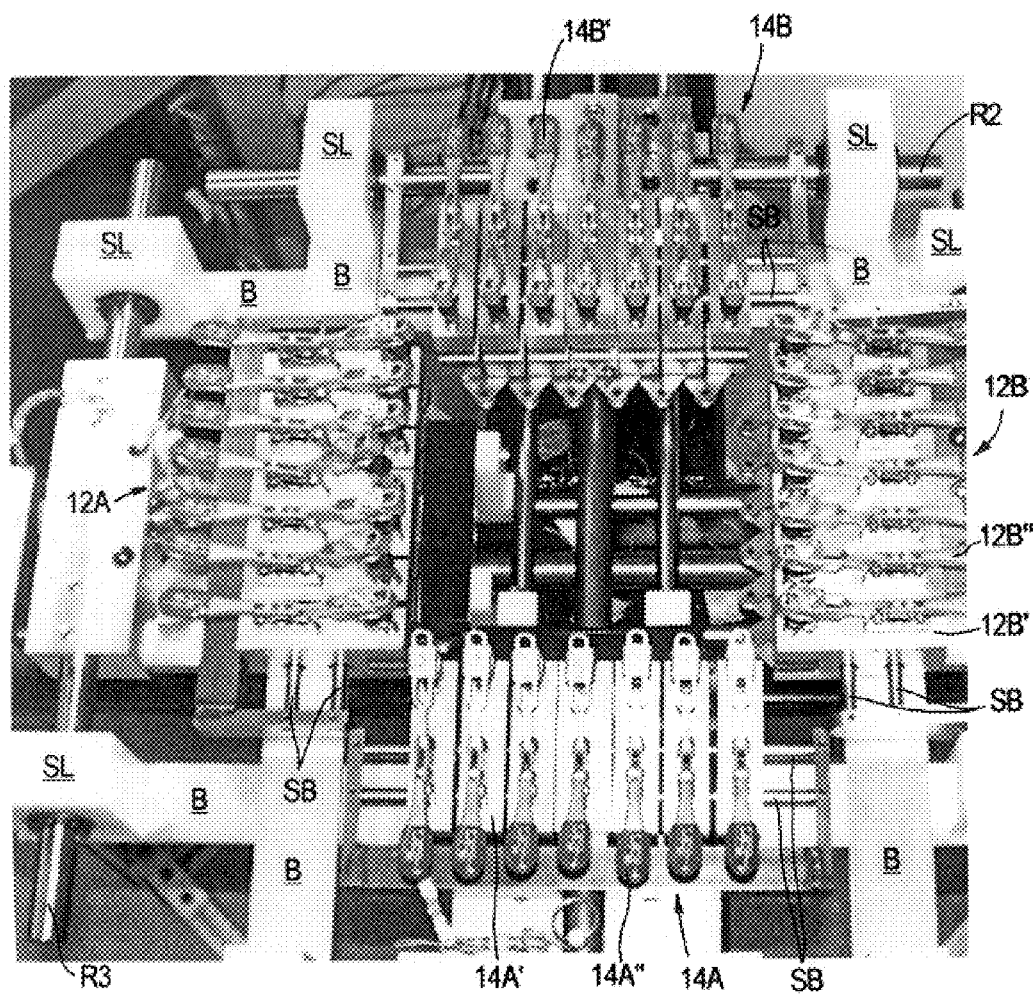
FIG. 6 is top perspective view of the apparatus of the present invention depicting both the first pair of spaced-apart segmented clamping systems extending in the X direction and the second pair of spaced-apart segmented clamping systems extending in the Y direction for engaging the four edges of a membrane test material.
Figure 7B:
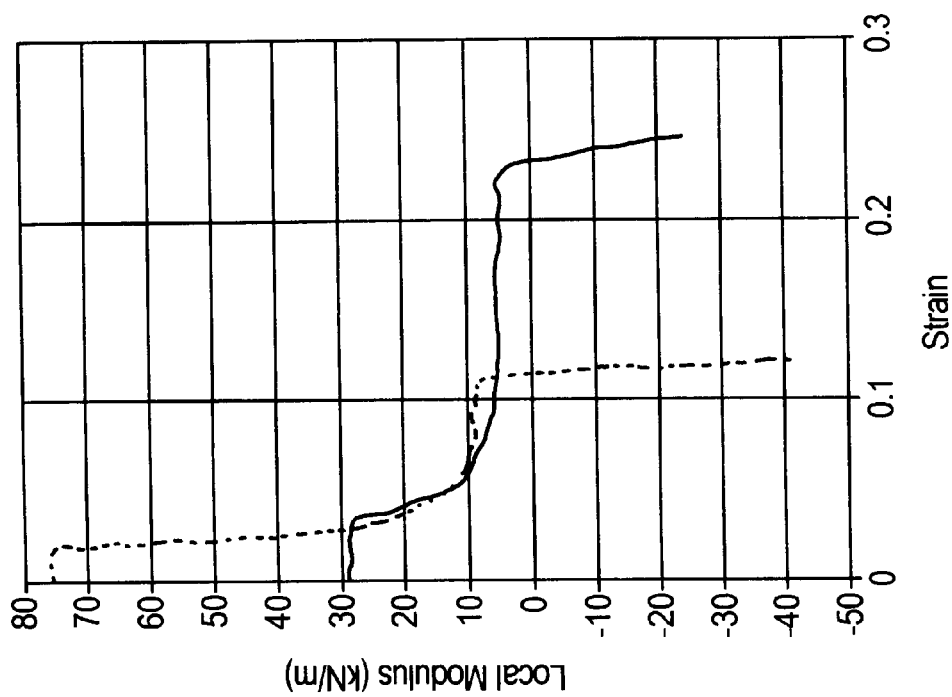
FIGS. 7A–7B is a stress/strain diagram (FIG. 7A) and a diagram of tensile modulus as a function of strain (FIG. 7B) of a spunbonded polyester fabric (50 g/m$^2$) measured at an extension ratio of 0.5.
Figure 7A:
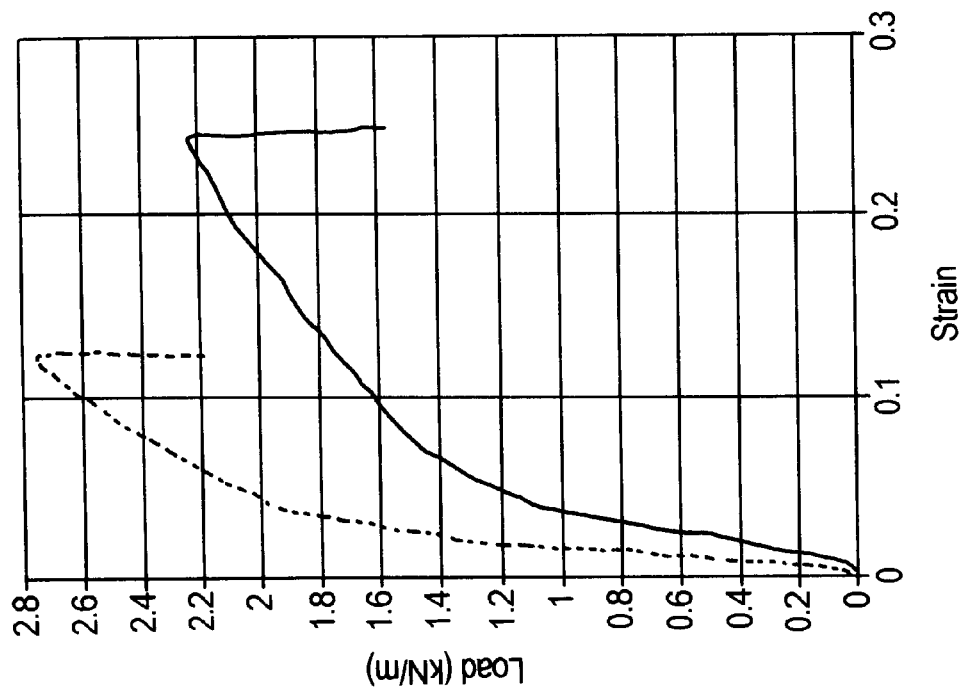
Figure 8B:
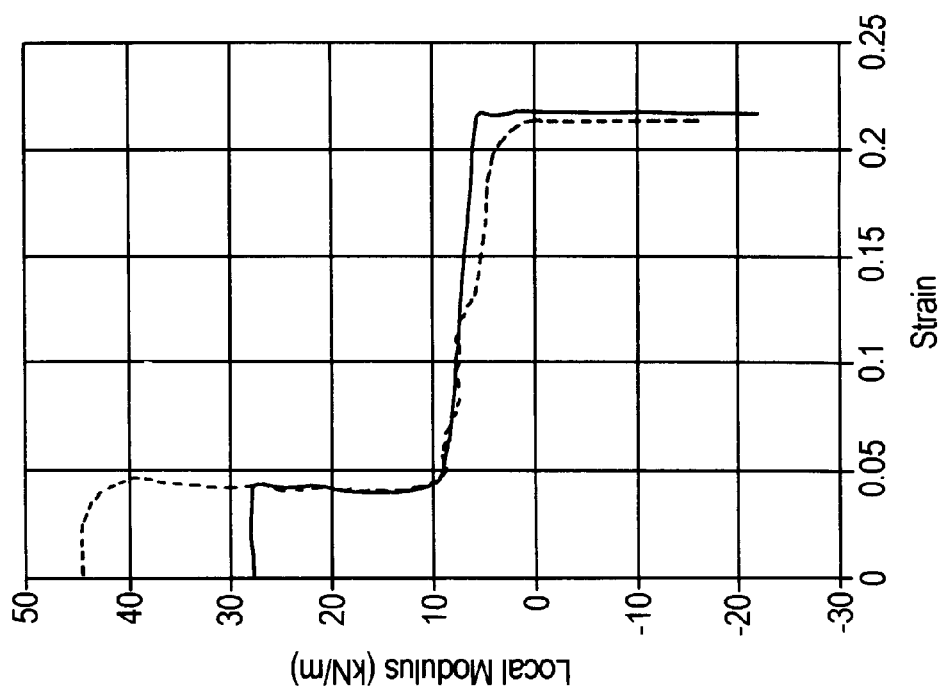
FIGS. 8A–8B is a stress/strain diagram (FIG. 8A) and a diagram of tensile modulus as a function of strain (FIG. 8B) of a spunbonded polyester fabric (50 g/m$^2$) measured at an extension ratio of 1.0.
Figure 8A:
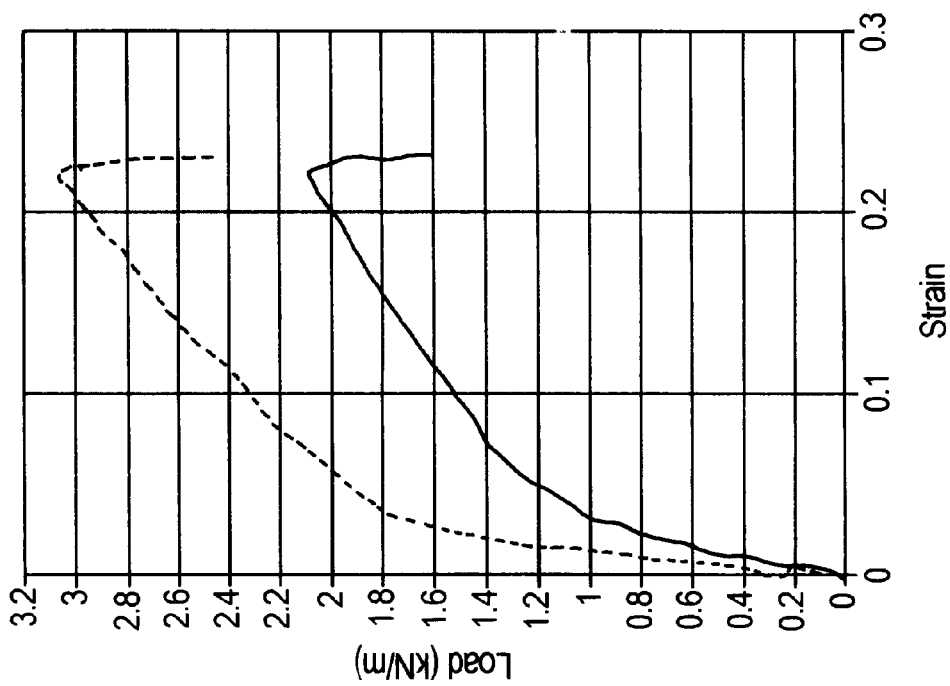
Figure 9B:
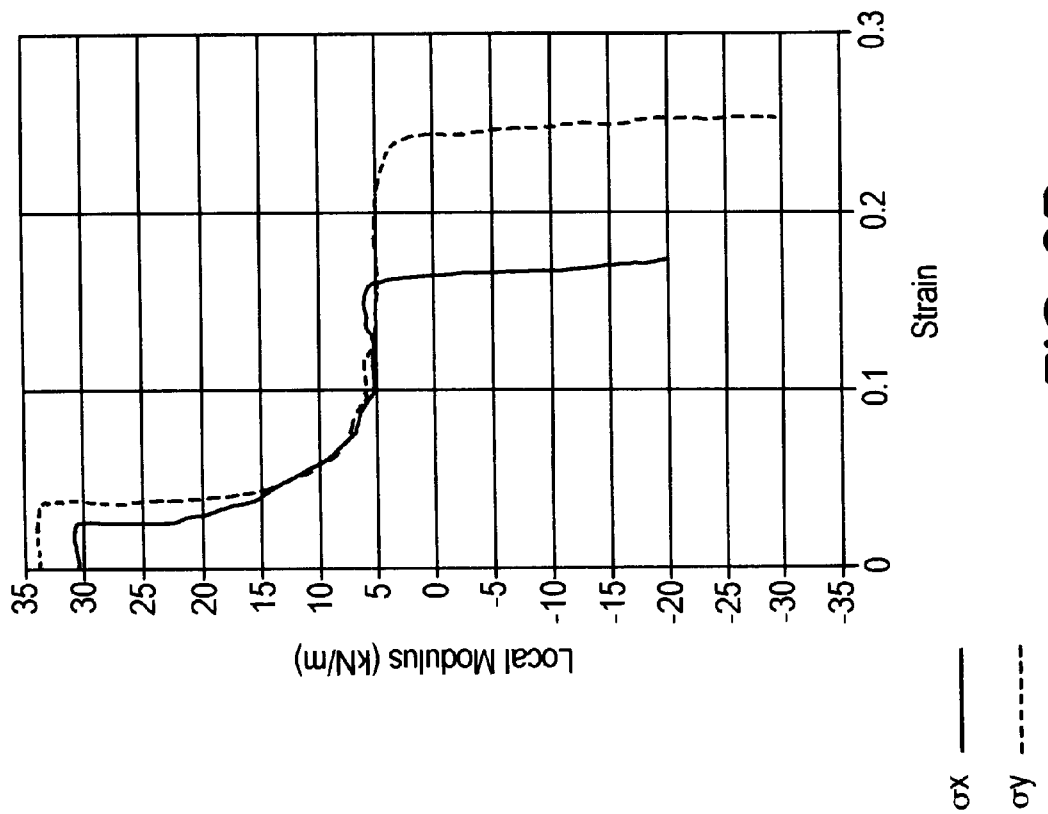
FIGS. 9A–9B is a stress/strain diagram (FIG. 9A) and a diagram of tensile modulus as a function of strain (FIG. 9B) of a spunbonded polyester fabric (50 g/m$^2$) measured at an extension ratio of 1.5.
Figure 9A:
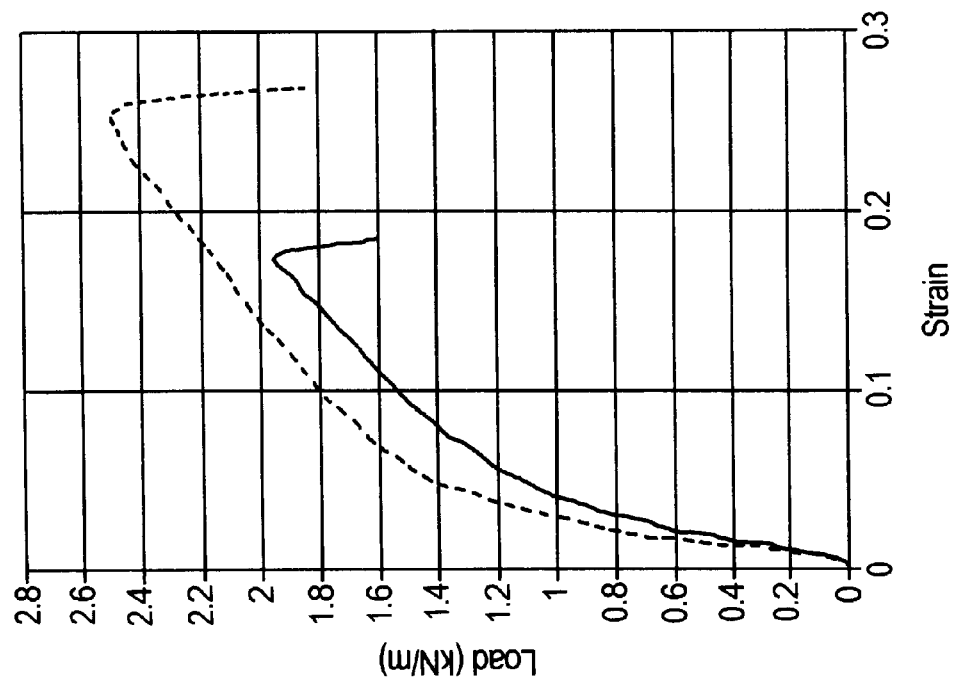
Figure 10B:
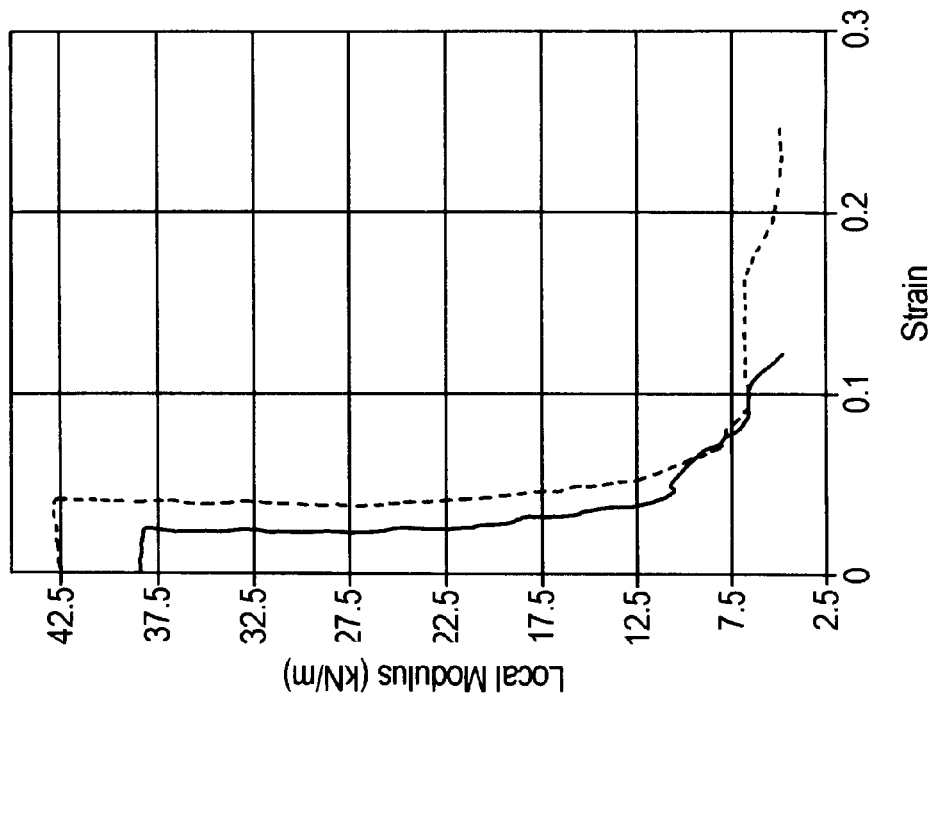
FIGS. 10A–10B is a stress/strain diagram (FIG. 10A) and a diagram of tensile modulus as a function of strain (FIG. 10B) of a spunbonded polyester fabric (50 g/m$^2$) measured at an extension ratio of 2.0.
Figure 10A:
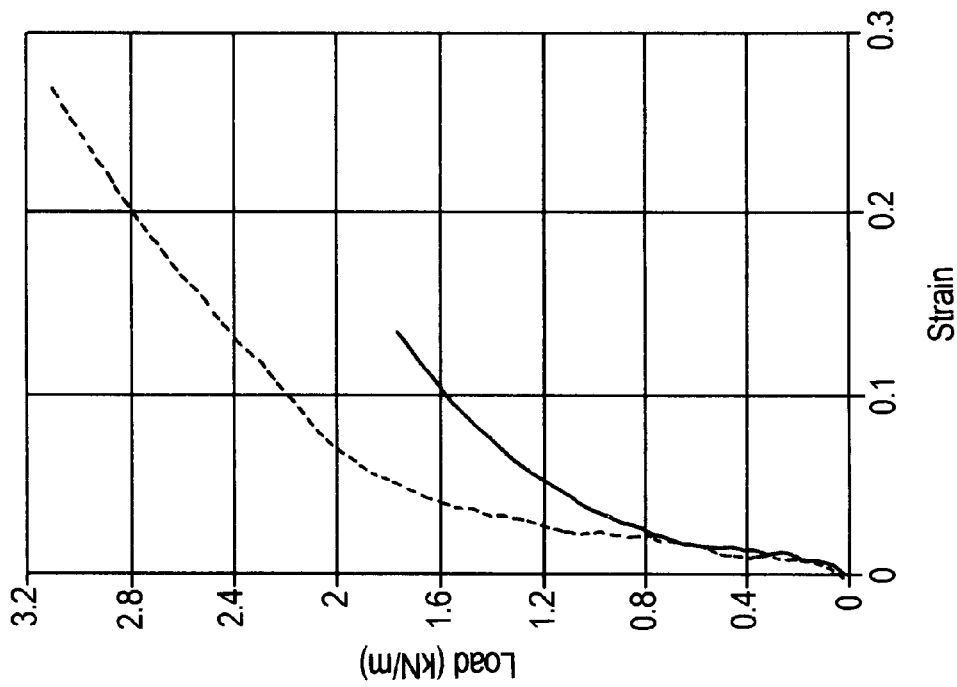

Referring now to the drawings, a preferred embodiment of applicant's biaxial deformable membrane testing apparatus and its method of use will be described in detail hereinafter. The testing apparatus, generally designated 10, is constructed with a first pair of spaced-apart segmented clamping systems 12A, 12B and a second pair of spaced-apart segmented clamping systems 14A, 14B. The first pair of segmented clamping systems 12A, 12B are adapted to be driven away from each other along the Y axis, and the second pair of clamping systems 14A, 14B are adapted to be driven apart from each other in the X axis direction (orthogonal to the Y axis) in a manner that will be described in more detail below. The first pair of segmented clamping systems 12A and 12B engage a membrane test material M along opposing edges that extend in the X direction, and the second pair of segmented clamping systems 14A, 14B engaging the remaining two opposing edges of test membrane M that extend in the Y direction.

Each one of the first pair of segmented clamping systems 12A, 12B and the second pair of segmented clamping systems 14A, 14B consist of seven segments 12A', 12B' and 14A', 14B', respectively, and each of the seven segments for each of the four segmented clamping systems (12A, 12B and 14A, 14B) has a spring-loaded clamp mounted thereon to hold a portion of the edge of test membrane M. For example, seven segments 12A' of clamping system 12A each include spring-loaded clamp 12A" mounted thereon. Correspondingly, each of the seven segments 12B' of clamping system 12B include spring-loaded clamp 12B" mounted thereon; each of the seven segments 14A' of clamping system 14A include a spring-loaded clamp 14A" thereon; and each of the seven segments 14B' of clamping system 14B include spring-loaded clamp 14B" mounted thereon.

Each one of the first pair of segmented clamping systems 12A, 12B and the second pair of clamping systems 14A, 14B is mounted on two parallel slider bars SB to facilitate substantially frictionless lateral motion by clamp segments 12A', 12B' and 14A', 14B' of corresponding clamping systems 12A, 12B and 14A, 14B. Each one of the first pair of segmented clamping systems 12A, 12B is connected underneath by a pantograph P. Pantograph P serves to allow clamp segments 12A', 12B' and 14A', 14B' of clamping systems 12A, 12B and 14A, 14B, respectively, to move apart from each other when test membrane M is strained in the Y direction (so as to cause clamping systems 14A, 14B to proportionally be extended apart) and when test membrane M is extended in the X direction (so as to cause elements 12A', 12B' of clamping systems 12A, 12B to extend apart a distance proportional to the strain imparted in the X direction to test membrane M).

As will be further appreciated by those skilled in the art, each of the pair of spaced-apart clamping systems 12A, 12B and each of the pair of spaced-apart clamping systems 14A, 14B is formed with the corresponding clamp segments 12A', 12B' and 14A', 14B', respectively, constructed so that the central clamp segment is stationary and serves as an anchor for its associated pair of slider bars SB and its associated pantograph P. Thus, for each of segmented clamping systems 12A, 12B and 14A, 14B the central clamp element of each set of seven clamp elements 12A', 12B' and 14A', 14B' is fixed so as to allow the three clamps on either side thereof to extend when test membrane M is strained so that each of the seven clamp segments for each of clamping systems 12A, 12B and 14A, 14B will be spaced an equal distance apart.

Referring again to the drawings, it will be appreciated that both of the first pair of segmented clamping assemblies 12A, 12B and both of the second pair of segmented clamping systems 14A, 14B are affixed to carriages which are slidably translated on a respective pair of guide rails GR, GR'. Thus, segmented clamping systems 12A, 12B rest in opposing relationship on a common pair of guide rails GR, and the second pair of segmented clamping systems 14A, 14B also commonly rest on a second pair of guide rails GR' in opposing relationship to each other. Clamping systems 12A, 12B are driven along guide rails GR in the Y direction by threaded screw S which extends the entire length of the machine so as to provide an optimal range of separation movement to clamping systems 12A, 12B. Correspondingly, clamping systems 14A, 14B are driven by threaded screw S' in the X direction of movement across the entire apparatus 10 so as to provide optimal range of movement to opposing clamping systems 14A, 14B. The threads of both drive screw S extending in the Y direction and drive screw S' extending in the X direction are created so as to threadingly extend clockwise for one half of the length of the screw and counterclockwise for the remaining half length of the screw. Thus, the first pair of segmented clamping systems 12A, 12B rest on opposing ends of drive screw S, and the second pair of segmented clamping systems 14A, 14B rest on opposite ends of drive screw S'. In this manner, rotation of drive screw S serves to move segmented clamping systems 12A, 12B in opposite directions with equal displacement either toward or away from each other, and rotation of drive screw S' serves to move the second pair of segmented clamping systems 14A, 14B in opposite directions with equal displacement toward or away from each other. It will be appreciated with reference to the drawings that the Y direction and X direction movements of segmented clamping systems 12A, 12B and 14A, 14B are mutually perpendicular or orthogonal to each other.

Drive screw S is driven by stepper motor M1 through gear box G1. Stepper motor M1 is most suitably a SUPERIOR SLO-SYN brand stepper motor, Model No. M093-FF-402, available from Warner Electric Motors & Controls Division in South Beloit, Ill., and gear box G1 is most suitably a MORSE INDUSTRIAL CORP. brand gear box, Model No. SF113 1556C, available from Morse Industrial Corp. in Ithaca, N.Y. Also, drive screw S' is driven by stepper motor M2 through gear box G2 which are identical to stepper motor M1 and gear box G1 described hereinbefore. As will be understood by those skilled in the art, gear boxes G1, G2 serve to step down the rotational speed of corresponding stepper motors M1, M2 so as to impart a desired load and/or strain in the X and Y directions to test membrane M on apparatus 10.

Apparatus 10 serves to apply a known extension to test membrane M and to then measure its load response or to apply a known load to test membrane M and then measure its extension response. Irrespective of the test being applied to test membrane M in the Y and X directions, clamping systems 12A, 12B will proportionally respond to strain (elongation) in the Y direction by test membrane M and the second pair of segmented clamping systems 14A, 14B will proportionally respond to strain (elongation) in the X direction that is imparted to test membrane M so as to allow the four edges of test membrane M to be stretched proportionally and to obviate well-known undesirable boundary effects that occur in conventional biaxial deformation testing of membrane materials.

Referring again to the drawings, applicant will now describe the linkage system that serves to stretch apart or extend clamping systems 12A, 12B in the X direction proportional to the X direction elongation of test membrane M during testing and to extend clamping systems 14A, 14B proportional to the Y direction elongation of test membrane M during biaxial deformation testing with apparatus 10. For example, if test membrane M is strained or extended 5% in the Y direction and 10% in the X direction during testing by apparatus 10, the second pair of clamping systems 14A, 14B will extend 5% in the Y direction and the first pair of clamping systems 12A, 12B will extend 10% in the X direction corresponding to the strain or elongation of test membrane M. The ability of the novel clamping system of apparatus 10 to accommodate strain or elongation along all four edges of test membrane M during testing provides for a high degree of accuracy during biaxial deformation testing of test membrane M and serves to overcome the well-known boundary effect inherent in conventional biaxial deformation testing devices.

To accomplish the desired proportional extending of the first pair of segmented clamping systems 12A, 12B with X direction elongation or strain and the proportional extending of the second pair of segmented clamping systems 14A, 14B with Y direction elongation or strain of test membrane M, applicant again refers to the drawings and notes that each of clamping systems 12A, 12B are slidably connected at one end to slider rod R1 that extends in the Y direction through clamping system 14A, and each of segmented clamping systems 12A, 12B are connected at the other end to slider rod R2 that extends in the Y direction through clamping system 14B. Segmented clamping systems 12A, 12B are each slidably connected to slider rods R1, R2 (affixed to and extending through segmented clamping systems 14A, 14B, respectively) by means of a pair of connector bars B extending laterally outwardly from each side of each of clamping system 12A and clamping system 12B and each connector bar B terminating in slider bearing or sleeve SL that slidably translates along slider rods R1, R2. Thus, by way of further description, as segmented clamping systems 14A, 14B move apart from one another in the X direction, the corresponding movement apart of slider rods R1, R2 connected to segmented clamping systems 14A, 14B serves to extend clamping systems 12A, 12B apart a proportional distance by means of connector bars B that extend laterally outwardly from the first and last of segmented clamp elements 12A' of clamping system 12A and the first and last of clamping elements 12B' of clamping system 12B. As slider rods R1, R2 move apart in the X direction, they serve to pull apart the first and last clamp element of each of clamping systems 12A, 12B and this motion is transmitted through pantograph P associated with each of clamping systems 12A, 12B into equal movement of each of clamping elements 12A' of segmented clamping system 12A and 12B' of segmented clamping system 12B. Thus, X direction movement apart of segmented clamping systems 14A, 14B is translated into proportional extension of clamping systems 12A, 12B in the X direction by means of slider rods R1, R2 which impart the movement to clamping systems 12A, 12B through four bearing sleeves SL and four connector bars B which are in turn connected to the first and last clamp element of each of clamping systems 12A, 12B. It must be noted that slider rods R1, R2, R3 and R4 are placed in such a way so that the force exerted to cause displacement in pantographs P is not recorded by the load detection systems of apparatus 10.

Correspondingly, Y direction movement of segmented clamping systems 12A, 12B is proportionally translated to Y direction extension of clamping systems 14A, 14B through slider rods R3, R4 associated with segmented clamping systems 12A, 12B, respectively, and through corresponding bearing sleeves SL carried thereby and four connector bars B which serve to connect the first and last clamp element of both clamping systems 14A, 14B to slider rods R3, R4 by means of bearing sleeves SL. In this fashion, as clamping systems 12A, 12B are moved apart in the Y direction, the movement is proportionally translated to clamping systems 14A, 14B through slider rods R3, R4 and four associated bearing sleeves SL and connector bars B in order to cause segmented clamping systems 14A, 14B to proportionally extend by means of pantograph P interconnecting each clamping system. Thus, it will be appreciated that apparatus 10, when performing biaxial deformation upon a test membrane M so as (for example) to impart 5% strain in the Y direction and 10% strain in the X direction will act to extend clamping systems 14A, 14B 5% in the Y direction and corresponding clamping systems 12A, 12B 10% in the X direction.

Apparatus 10 can apply precise displacements and measure load response by means of load cell 16A mounted behind segmented clamping system 14A to measure load response in the X direction and load cell 16B mounted behind segmented clamping system 12A to measure load response in the Y direction. Further, strain or extension of test membrane M is measured by apparatus 10 through LVDT (linear variable differential transformer) 18A located at the end of drive screw S remote from gear box G1 and LVDT 18B located at the end of drive screw S' at the opposite end from gear box G2. LVDTs 18A, 18B serve to measure extension or strain in the Y direction and X direction, respectively, during testing of test membrane M. Most suitably, load cells 16A, 16B are ENTRAN brand, Model No. ELH-TC590-1000, available from Entran, Sensors & Electronics in Fairfield, N.J., and LVDTs 18A, 18B are RDP ELECTRONICS brand, Model No. DCT1000A, available from RDP Electronics.

Most suitably, apparatus 10 is controlled through a computer, preferably a DELL brand personal computer, Model No. XTPS, available from Dell, which in turn is in electrical connection with load cells 16A, 16B, LVDTs 18A, 18B and stepper motors M1, M2 in order for proper data to be acquired by the computer to control operation of apparatus 10 in accordance with predetermined parameters.

It should be appreciated that although applicant has tested apparatus 10 on textile membranes as will be described in more detail hereinafter, applicant contemplates that apparatus 10 can be used for biaxial deformation testing of virtually any type of deformable membrane including woven textiles, nonwoven textiles, geotextiles, films, reinforced films, polymeric films, soft composites, coated laminates and the like.

A critical feature incorporated in apparatus 10 is the force or extension programming. In a uniaxial test, the control variable is either the force or extension. Commonly, although not always, the rate of change of one of these is held constant, resulting in a constant rate of loading or constant rate of elongation machine. The two variables are, of course, not independent; either having been programmed and the other is the result. In a biaxial test, the situation is significantly more complicated due to the increased number of variables and the interaction of yarn systems in the two principal directions of the fabric membrane. It can be shown that the force-extension programming in biaxial testing must consist of simultaneous specification of either both forces or both extensions. Therefore, apparatus 10 is designed to control either of the ratios of force ($\sigma_y/\sigma_x$) or extensions ($\epsilon_y/\epsilon_x$) during an experiment. During a test, appropriate displacements are applied to the sample edges while either of force or extension ratios is held constant through a feedback control loop in the control system. The test results are obtained in the form of force-extension diagrams for both machine and cross directions of the test sample as will be described im detail hereinbelow.

A. Method of Use

Mounting the sample for testing:

A test sample of fabric/nonwoven material M is cut to size (27.5 cm×27.5 cm). The sample is held along all four edges and is kept relatively taut so as to avoid any slack. Small cuts are then made between the segments (the cut extends from the edge of the sample to the edge of the test area, i.e., the depth of the segment in which it is clamped). These will allow for the free movement of the segments and the pantograph as the test is carried out and the edges lengthen.

The sample M is held on all four edges by four sets or systems of segmented clamps (12A, 12B and 14A, 14B). Every edge has seven clamp segments that form a clamp system. Each clamp segment has a spring-loaded clamp to hold a part of test sample M. Two parallel slider bars SB run through the seven segmented clamps and hold them up and provide frictionless motion along their length. The clamp segments of each clamp system are connected underneath by a pantograph P. This allows the segments to move apart in proportion to applied deformation when sample M is stretched. The central clamp segment of each clamp system is stationary and is the anchor for slider bars SB and pantograph P. Three clamps are on either side of the central clamp segment.

The two pairs of segmented edge clamp assemblies (12A, 12B and 14A, 14B) sit on carriages which run on two respective guide rails GR, GR'. Opposing edge clamp assemblies sit on two carriages running along the same set of guide rails GR, GR', respectively (the X or the Y axis). The carriages of each opposing pair of clamp assemblies are driven by a respective threaded screw S, S' which runs the entire length of the axis, giving the carriages an optimum range of movement. The threads of drive screws S, S' are clockwise for one half length of the axis and counterclockwise on the other. The two clamp system carriages per axis each sit on half of a corresponding drive screw S, S'. Every revolution of drive screws S, S' moves the two respective carriages in opposite directions with equal displacements.

The initial configuration of apparatus 10 is with the four clamp edges closest to each other so as to create a small square (22.5 cm×22.5 cm). The test sample M is mounted at this time. The carriages carrying clamp systems 12A, 12B and. 14A, 14B along each axis sit close to the center of the axis and each other. This is also the closest formation of pantographs P linked to the segment clamps. Stepper motors M1, M2 drive the threaded screw S, S' associated with each axis. These motors are designed to provide a high torque at a high speed. The speed of stepper motors M1, M2 is stepped down via corresponding gear boxes G1, G2. The motors and the gear box are at the end of each axis.

Testing the sample.

Apparatus 10 applies a known extension to the test sample and then measures its load response. The sample M is stretched between the edge clamps by moving the carriages for the clamp assemblies apart. Very precise displacements can be applied and the load response can be measured by load cells 16A, 16B mounted behind the clamp assembly for each axis. The stepper motors M1, M2 are moved by an operator-specified amount as well as rate. These turn the threaded drive screws S, S' moving the carriages through equal distances and opposite directions. The carriages move outward and away from each other. The outer limit is the position of the clamp assemblies at their furthest apart along each axis. This outer limit also coincides with the furthest expansion of the pantographs P. (At this position, the test sample M would be at the greatest deformation and hence the edges would be at the longest.) The recovery phase is the return to the initial position. Motors M1, M2 reverse their direction of rotation and the drive screws S, S' move their respective pair of carriages inwards and towards each other until the initial position has been reached.

The extension of the test sample is measured by LVDTs (Linear Variable Differential Transformer) 18A, 18B located at the end of the axes. Since the carriages are moving an equal amount from each other, only one carriage per axis has its displacement measured. LVDTs 18A, 18B also serve to warn the controlling software when the displacement limits of the carriages along the axes are reached. These limits are critical since motors M1, M2 are powerful enough to inflict serious damage on the more delicate components if they are not used within the design envelope.

The load measurements are read using load cells mounted behind one of the carriages per axis. This particular carriage is connected to the edge clamp assembly through the load cell. It is very important to have no side loads on this clamp assembly.

To ensure that only the load from the test sample being extended is measured, and not the load from the pulling apart of clamp segments, this load is diverted to behind the load cell. The sliders with a reinforcing yoke are shown in the drawings. All the operations are controlled using a computer as described above. The stepper motor controllers, amplifiers for the load cell signals and LVDT are the hardware used to feed data into the computer via data acquisition cards.

B. Test Results and Discussion

Initially, apparatus 10 was tested using a number of commercially available spunbonded nonwoven fabrics of a range of mass per unit area. In evaluating the load-frame and the control system of the BTI, fabrics were tested on a constant rate of extension (CRE) type tensile testing machine and on applicant's apparatus 10 in uniaxial mode. The fabrics were tested in both directions (X and Y) of the applicant's apparatus and force-extension diagrams were compared with that obtained from the CRE-type uniaxial tensile tester. There were no significant differences between the results. Subsequently, a number of these polyester spun-bonded fabrics were tested on the BTI using various force and extension ratios in biaxial mode. These fabrics are identified as PET1 (30 g/m$^2$), PET2 (50 g/m$^2$), and PET3 (70 g/m$^2$). As mentioned earlier, applicant's apparatus 10 is designed for both constant force ratio and extension ratio testing. However, in testing the fabrics selected for this study (PET1–PET3), it became evident that for constant force ratio testing, applicant's apparatus' limiting extension (28%) must be increased for practical use. None of the fabrics could be tested to failure under constant rate of loading conditions because the failure extensions are in excess of 28% at least for one of the sample directions. Therefore, the results reported here are from constant extension ratio tests. The crosshead speed on applicant's apparatus 10 along one direction (X) was kept at 8 cm/min, while the speed along the other direction varied according to the extension ratio specified for the test. It is important to note that all the test samples were conditioned and tested in a standard laboratory environment (20°±2° C. and 65±2% relative humidity).

Typical results of biaxial tests of a number of these samples are presented in FIGS. 7–13. In all cases, the fabric sample was tested with its longitudinal (machine) direction aligned with the Y-direction of applicant's apparatus. FIGS. 7–13 include force extension diagrams as well as their slopes or moduli plotted as functions of the strain.

The results of these tests are presented below and the influence of the extension ratio on fabric behavior will be discussed in terms of failure stress and extension as well as initial tensile modulus of the fabrics in both machine and cross directions. Initial modulus in this context is defined as the slope of the stress strain curve between 0 and 25% of the failure strain. Also, note that in all cases the number of samples tested were four. Therefore, each data point in the plots below is the average of four test samples.

Figure 11A:
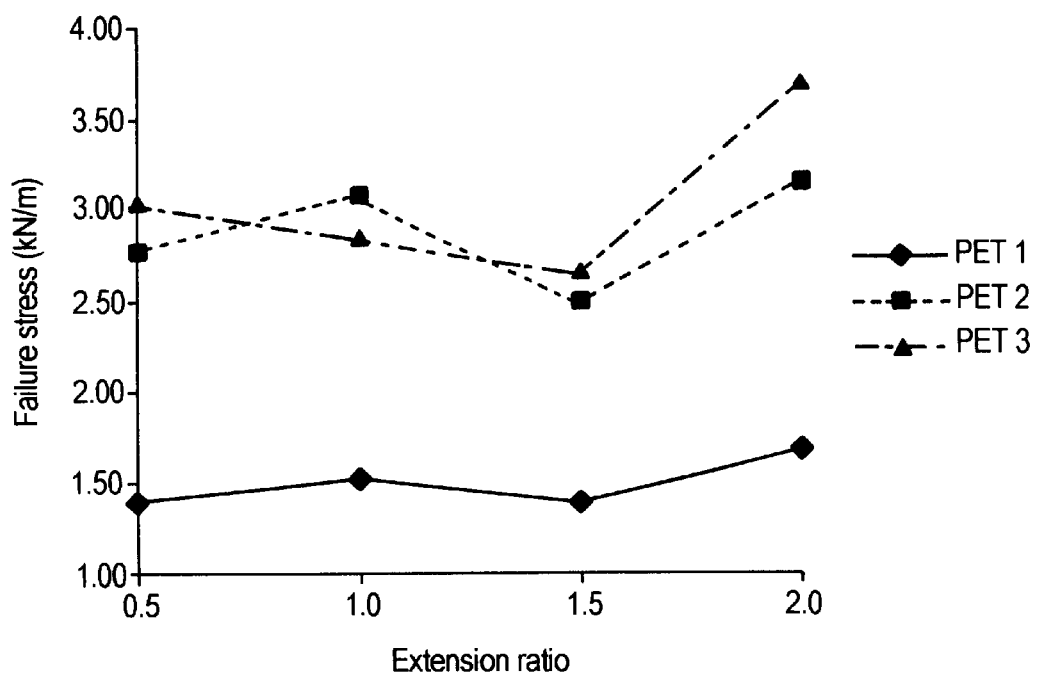
FIGS. 11A–11B is a graph illustrating the variation of failure stress in the machine direction (FIG. 11A) and in the cross direction (FIG. 11B) as a function of extension ratio.
Figure 11B:
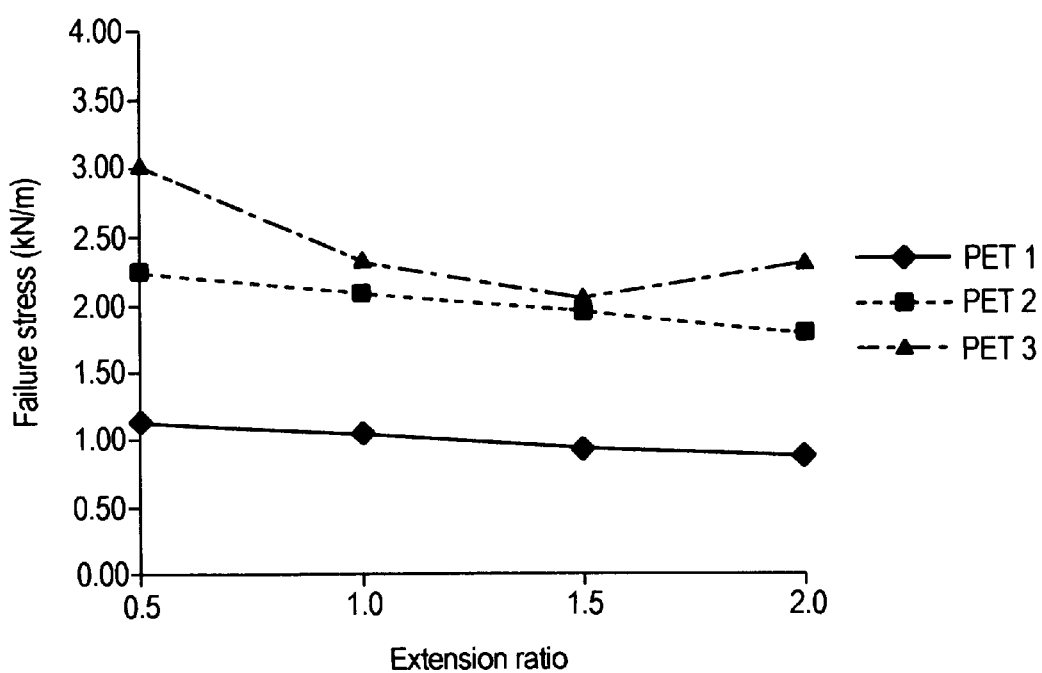
Figure 12A:
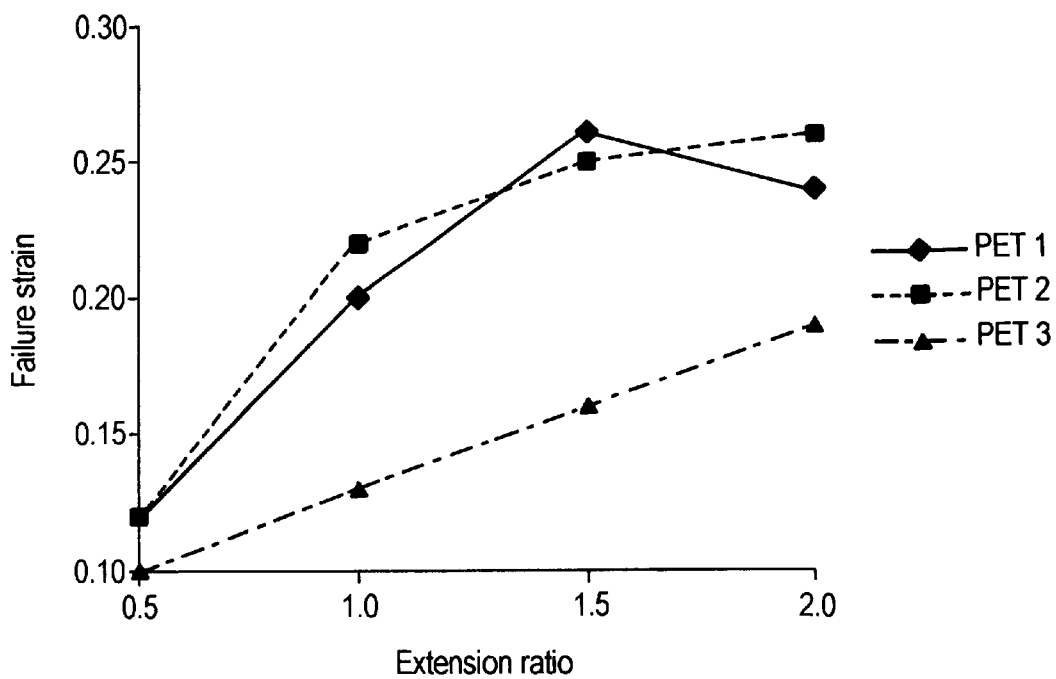
FIGS. 12A–12B is a graph illustrating the variation of failure strain in the machine direction (FIG. 12A) and in the cross direction (FIG. 12B) as a function of extension ratio.
Figure 12B:
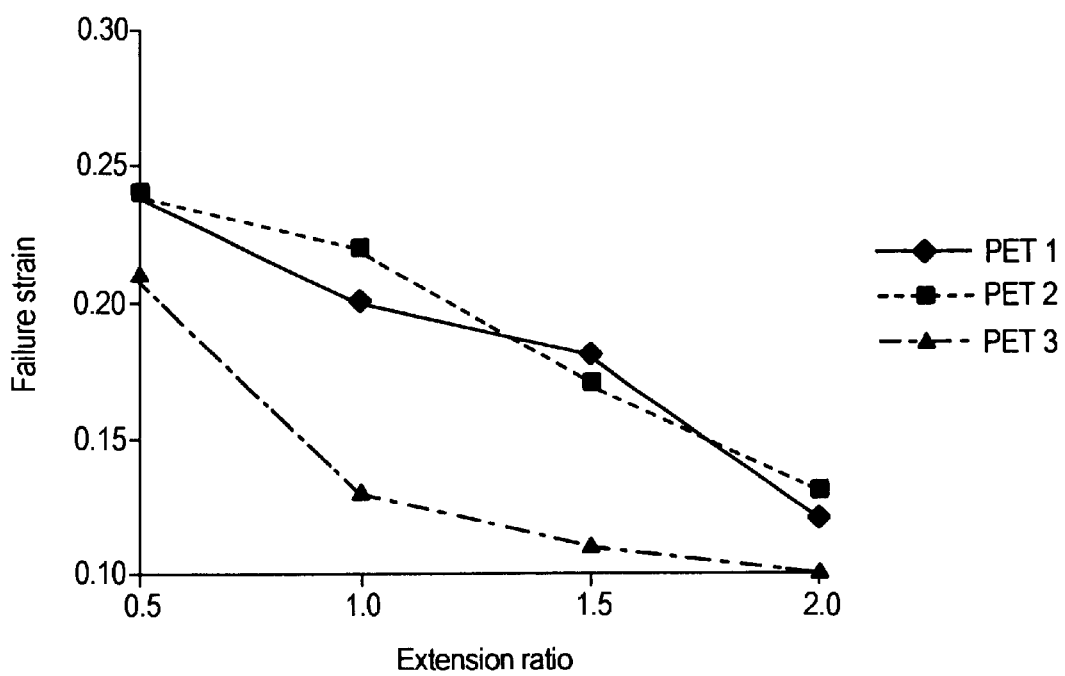

In constant extension ratio tests, the extension ratio ($\epsilon_y/\epsilon_x$) was held constant at various levels (0.5, 1.0, 1.5, and 2.0) during the tests. FIGS. 11A and 11B show the failure stress of the test fabrics as a function of extension ratio, in machine and cross directions, respectively. Similarly, FIGS. 12A and 12B show failure strains in the machine and cross directions as a function of increasing extension ratio. The failure stress values do not clearly indicate any trend. However, for higher extension ratios, the failure strain is clearly higher in the machine direction while the opposite is true of the cross direction. It is important to recall that in all cases tests were performed with fabric machine direction aligned with Y-direction of the BTI. Therefore, higher extension ratio means larger relative deformation in the Y-direction of the BTI or machine direction of the fabric. In other words, the higher extension ratio also means less constraint imposed in the cross direction of the fabric. As a result, the experimental data clearly show increased failure stress and strain in the machine direction, while the opposite is observed in the cross direction.

Figure 13A:
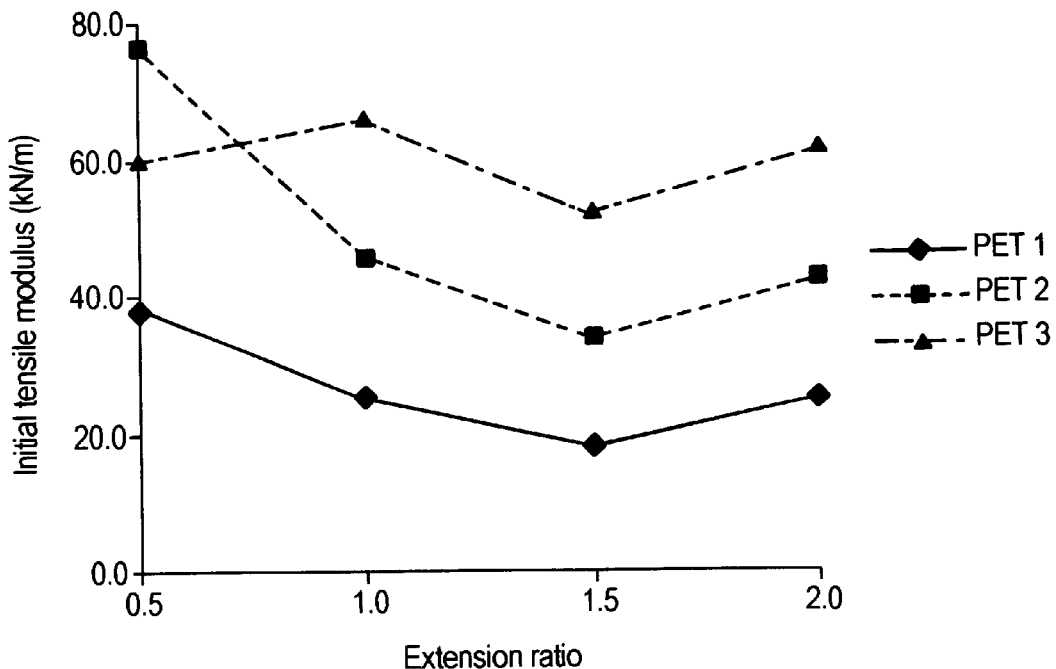
FIGS. 13A–13B is a graph illustrating the variation of initial tensile modulus in the machine direction (FIG. 13A) and in the cross direction (FIG. 13B) as a function of extension ratio.
Figure 13B:
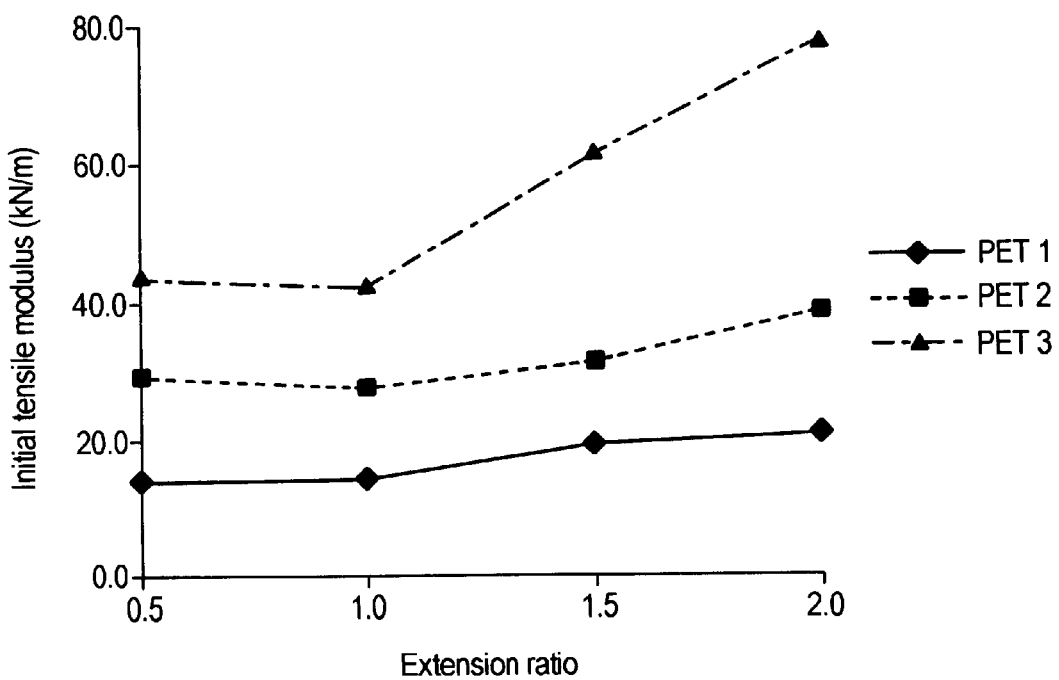

Tensile modulus is a measure of the resistance of the fabric to deformation and is an important parameter in many applications. As mentioned earlier, the initial modulus in this study is defined as the slope of the stress-strain curve between 0 to 25% of the failure strain of the fabric. The choice is somewhat arbitrary, but is based on the experimental observation that the stress-strain curves are fairly linear in this range. FIGS. 13A and 13B show the variation of fabric initial modulus with extension ratio for machine and cross directions. In most cases, the initial modulus in the machine direction goes down with higher extension ratios, while in the cross direction the initial modulus values go up. Once again, at higher extension ratios, the machine direction strain is higher and thereby it imposes a higher level of constraint to the fiber movement along the cross direction to accommodate cross direction extension. Therefore, the fabric is more rigid in the cross direction with higher extension ratio.

The test results clearly show the importance of biaxial deformation in determining fabric stress-strain characteristics. The failure characteristics as well as the fabric moduli in any one of the principal fabric directions are significantly altered by the presence of constraints in the other direction. In almost any fibrous structure, and in particular, in nonwoven fabrics, the strain in any direction results in increasing fiber alignment along the direction of the strain. The resistance encountered during this fiber realignment or movement is proportional to the constraint (force or strain) applied in the direction normal to the direction of deformation. In turn, this resistance determines the rigidity of the fabric in the direction of measurement. A higher degree of freedom of fiber movement results in lower fabric rigidity.

It will be understood that various details of the invention may be changed without departing from the scope of the invention. Furthermore, the foregoing description is for the purpose of illustration only, and not for the purpose of limitation—the invention being defined by the claims.

What is claimed is:

1. An apparatus for biaxial load deformation testing of textile and membrane materials, said apparatus comprising:
   (a) a first pair of spaced-apart segmented clamping systems for detachably engaging a membrane test material along opposing sides extending in a first (X) direction, said clamping systems each comprising a plurality of clamps interconnected by a pantograph and slidably extendable and slidably contractible with respect to each other;
   (b) a second pair of spaced-apart segmented clamping systems for detachably engaging a membrane test material along opposing sides extending in a second (Y) direction, orthogonal to said first direction, said clamping systems each comprising a plurality of clamps interconnected by a pantograph and slidably extendable and slidably contractible with respect to each other;
   (c) a first drive system for moving said first pair of segmented clamping systems apart each from each other so as to impart a predetermined stress and/or strain in the second (Y) direction, and a second drive system for moving said second pair of segmented clamping systems apart each from each other so as to impart a predetermined stress and/or strain in the first (X) direction;
   (d) a first linkage system operatively interconnecting said first and second pair of segmented clamping systems so as to slidably extend said second pair of segmented clamping systems in the second (Y) direction proportional to strain imparted to a membrane test material in the second (Y) direction when said first pair of segmented clamping systems is caused to move apart in the second (Y) direction by said first drive system; and
   (e) a second linkage system operatively interconnecting said first and second pair of segmented clamping systems so as to slidably extend said first pair of segmented clamping systems in the first (X) direction proportional to strain imparted to a test membrane in the first (X) direction when said second pair of clamping systems is caused to move apart in the first (X) direction by said second drive system.

2. The apparatus according to claim 1, including first and second load cells operatively connected to said first and second pairs of segmented clamping systems, respectively, to measure a load being imparted to a membrane test material in the first (X) and second (Y) directions by said first and second pairs of segmented clamping systems, respectively.

3. The apparatus according to claim 2, including first and second LVDTs operatively connected to said first and second pairs of segmented clamping systems, respectively, to measure the extension being imparted to a membrane test material in the first (X) and second (Y) directions by said first and second pairs of segmented clamping systems, respectively.

4. The apparatus according to claim 3, including a control system operatively connected to said first and second drive systems, said first and second load cells and said first and second LVDTs.

5. The apparatus according to claim 4, wherein said control system comprises a computer with suitably programmed control software for controlled tests of a membrane test material.

6. The apparatus according to claim 1, wherein said clamping systems each comprise 7 clamps interconnected by a pantograph so that 3 clamps on each side of a stationary center clamp are slidably extendable and slidably contractible with respect to said stationary center clamp.

7. The apparatus according to claim 6, wherein the plurality of clamps for each one of said first pair of segmented clamping systems is slidably mounted on 2 parallel slide bars extending in the first direction, and the plurality of clamps for each one of said second pair of segmented clamping systems is slidably mounted on 2 parallel slid bars extending in the orthogonal second direction.

8. The apparatus according to claim 1, wherein said first and second drive systems each comprise a stepper motor and threaded screw for imparting the predetermined stress and/or strain in the second (Y) and first (X) directions, respectively, to a membrane test material.

9. A method for biaxial load deformation testing of textile and other membrane materials, said method comprising the steps of:
   (a) providing a first pair of spaced-apart segmented clamping systems for detachably engaging a membrane test material along opposing sides extending in a first (X) direction, said clamping systems each comprising a plurality of clamps pantographically interconnected and slidably extendable and slidably contractible with respect to each other;
   (b) providing a second pair of spaced-apart segmented clamping systems for detachably engaging a membrane test material along opposing sides extending in a second (Y) direction, orthogonal to said first direction, said clamping systems each comprising a plurality of clamps pantographically interconnected and slidably extendable and slidably contractible with respect to each other;
   (c) driving said first pair of segmented clamping systems apart from each other to impart a predetermined stress and/or strain in the second (Y) direction and thereby causing said operatively connected second pair of segmented clamping systems to slidably extend in the second (Y) direction proportional to the strain imparted to a membrane test material in the second (Y) direction; and (d) driving said second pair of segmented clamping systems apart from each other to impart a predetermined stress and/or strain in the first (X) direction and thereby causing said operatively connected first pair of segmented clamping systems to slidably extend in the first (X) direction proportional to the strain imparted to a membrane test material in the first (X) direction.

10. The method according to claim 9, including measuring a load being imparted to a membrane test material in the first (X) and second (Y) directions by said first and second pairs of segmented clamping systems, respectively.

11. The method according to claim 10, including providing first and second load cells operatively connected to said first and second pairs of segmented clamping systems, respectively, to measure a load being imparted to a membrane test material.

12. The method according to claim 9, including measuring the extension being imparted to a membrane test material in the first (X) and second (Y) directions by said first and second pairs of segmented clamping systems, respectively.

13. The method according to claim 12, including using first and second LVDTs operatively connected to said first and second pairs of segmented clamping systems, respectively, to measure the extension being imparted to a membrane test material.

14. The method according to claim 9, including selecting the membrane material to be tested from a group consisting of woven textiles, non-woven textiles, geotextiles, films, polymeric films, reinforced films, soft composites, and coated laminates.

* * * * *